US006136606A

United States Patent [19]

Chatfield

[11] Patent Number: 6,136,606

[45] Date of Patent: Oct. 24, 2000

[54] INFLUENZA VACCINE COMPOSITIONS

[75] Inventor: Steven Neville Chatfield, London, United Kingdom

[73] Assignee: Medeva Holdings BV, Amsterdam, Netherlands

[21] Appl. No.: 09/066,340

[22] PCT Filed: Nov. 1, 1996

[86] PCT No.: PCT/GB96/02680

§ 371 Date: Apr. 29, 1998

§ 102(e) Date: Apr. 29, 1998

[87] PCT Pub. No.: WO97/16208

PCT Pub. Date: May 9, 1997

[30] Foreign Application Priority Data

Nov. 1, 1995 [GB] United Kingdom .................. 9522351

[51] Int. Cl.[7] .................................................. G01N 33/53

[52] U.S. Cl. .................... 435/975; 424/78.08; 424/94.1; 424/184.1; 424/206.1; 435/236; 435/238; 514/55; 514/888; 530/387; 530/404; 530/406; 530/413

[58] Field of Search .................................. 435/236, 238, 435/975; 514/55, 888; 530/806, 825, 387, 404, 406, 413; 424/78.08, 94.1, 184.1, 206.1

[56] References Cited

U.S. PATENT DOCUMENTS

| | | | |
|---|---|---|---|
| 4,659,569 | 4/1987 | Mitsuhashi et al. . | |
| 5,629,011 | 5/1997 | Illum . | |
| 5,700,459 | 12/1997 | Krone et al. | 424/78.08 |
| 5,891,992 | 4/1999 | Stevens | 530/317 |

FOREIGN PATENT DOCUMENTS

| | | |
|---|---|---|
| 0 183 556 A2 | of 1986 | European Pat. Off. . |
| 0 506 326 A3 | of 1992 | European Pat. Off. . |
| 0 460 020 B1 | of 1994 | European Pat. Off. . |
| 5163161 | of 1993 | Japan . |
| 6166635 | of 1994 | Japan . |
| 2 231 495 | of 1991 | United Kingdom . |
| WO 89/03207 | of 1989 | WIPO . |
| WO 90/09780 | of 1990 | WIPO . |
| WO 96/10421 | of 1996 | WIPO . |

OTHER PUBLICATIONS de Haan et al. "Mucosal immunoadjuvant activity of liposomes: induction of systemic IgG and secretory IgA responses in mice by intranasal immunization with an influenza subunit vaccine and coadministered liposomes" *Vaccine 13* (2), 155–162 (1995).

Oka et al. "Enhancing effects of pertussis toxin B oligomer on the immunogenicity of influenza vaccine administered intranasally" *Vaccine 12* (14), 125–1258 (1994).

Iida et al. "Stimulation of non–specific host resistance against Sendai virus and *Escherichia coli* infections by chitin derivatives in mice" *Vaccine 5,* 270–273 (1987).

Nishimura et al. "Immunological activity of chitin and its derivatives" *Vaccine 2,* 93–99 (1984).

Nishimura et al. "Effect of multiporous microspheres derived from chitin and partially deacetylated chitin on the activation of mouse peritoneal macrophages" *Vaccine 5,* 136–140 (1987).

S. Renfrey and A. Watts "Morphological and biochemical characterization of influenza vaccines commercially available in the United Kingdom" *Vaccine 12* (*8*), 747–752 (1994).

Indulen, M.K. et al. "The antiviral action of a modified bacterial ribonuclease" *Biol Nauki* (*Byelarus*) *4,* 87–89 (1992) (Abstract only).

Nishimura et al. "Adjuvant activity of chitin derivatives in mice and guinea–pigs" *Vaccine 3,* 379–384 (1985).

*Primary Examiner*—James O. Wilson
*Attorney, Agent, or Firm*—Heslin & Rothenberg, P.C.

[57] ABSTRACT

The invention provides a vaccine composition in the form of a kit, comprising a first container containing an antigenic preparation comprising influenza antigen or antigens; and a second container containing an effective adjuvant amount of a chitosan which is a deacetylated chitin which is at least 80% deacetylated. The antigenic preparation in the first container preferably comprises haemagglutinin and neuraminidase influenza antigens.

21 Claims, 4 Drawing Sheets

Effect of chitosan on nasal and pulmonary immunogenicity of flu purified surface antigen - ELISPOT Effect of chitosan on nasal and pulmonary immunogenicity of whole flu virus - ELISPOT
Anti A/Texas response
IgA
IgG
IgM
NOSES
LUNGS
ASC/10^7 Lymphocytes
8000
6000
4000
2000
4000
2000
WIV + Chit
prior
WIV + Chit
admix
WIV I/N

INFLUENZA VACCINE COMPOSITIONS

The invention relates to a vaccine composition in the form of a kit comprising a first container containing an antigenic preparation comprising influenza virus antigens and a second container containing a mucosal adjuvant. The invention also relates to a method of immunising a patient against influenza by administering the said composition to the patient, and a method of enhancing the immunogenicity of an influenza viral antigen, particularly when administered intranasally, by co-administering therewith the said adjuvant.

Current influenza vaccines consist of either inactivated whole virus, disrupted virus (split vaccines) or purified preparations of the membrane glycoproteins haemagglutinin (HA) and neuraminidase (NA) sub-unit vaccines. Haemagglutinin and neuraminidase are the antigens to which protective antibody responses are directed, haemagglutinin being the major protective antigen. Estimates of the efficacy of these parenterally administered vaccines vary greatly. Such vaccines are believed to act primarily by eliciting circulating anti-haemagglutinin lgG antibodies that transudate into the lower respiratory tract.

M. L. Clements et al, J. Clinical Microbiology 24, 157–160, 1986, have previously reported that both secretory IgA and serum lgG participate in immunity to influenza virus. Moreover, in mice, a number of published studies have demonstrated the importance of respiratory IgA to protection against influenza infection. It has also been found that an advantage of stimulating a local IgA response to influenza is that it is often of a broader specificity than the serum response and thus can provide cross-protection against viruses possessing haemagglutinin molecules different from those present in the vaccine. Accordingly, influenza vaccines that elicit both local secretory and serum anti-haemagglutinin responses should provide superior immunity to current vaccines. However, parenteral vaccination (intramuscular, sub-cutaneous etc) is not effective at eliciting local antibody production, if there has been no previous mucosal exposure (e.g. infection). In order to stimulate the mucosal immune system, the vaccine must be applied topically to a mucosal surface.

Mucosal administration of influenza vaccine would have a number of advantages over traditional parenteral immunisation regimes. Paramount amongst these are more effective stimulation of the local mucosal immune system of the respiratory tract and the likelihood that vaccine uptake rates would be increased because the fear and discomfort associated with injections would be avoided. Accordingly, a number of attempts have been made to develop mucosal influenza vaccines. A drawback however is that inactivated vaccines are often poorly immunogenic when given mucosally. For example, Kuno-sakai et al (vaccine 12:1303–1310, (1994) have shown that administration of inactivated vaccine to humans gave strong mucosal and serum antibody responses and was effective in preventing infection by live vaccine virus. However, in order to achieve such results, Kuno-sakai et al administered three times the commercially available dose, an approach which is not considered to be commercially viable. In order to overcome this problem, different approaches to improving the immunogenicity of flu vaccines given orally or intranasally have included the use of the B sub-unit of cholera toxin (CTB) as an adjuvant (see S. Tamura et al, vaccine, 6, 409, (1988), encapsulation of the vaccine in a variety of microspheres (see Z. Moldoveanu et al, J.lnf.Dis. 167, 85–90 (1993), and the use of live attenuated strains (see H. F. Maassab et al, vaccines, Plotkin S. A and Mortimer F. A Jr (eds) W. B. Saunders Philadelphia p435 (1993). To date however, no practical means of enhancing the immunogenicity of mucosally administered flu vaccines has been developed.

It has now been found by the Applicants that by administering influenza antigens such as the haemagglutinin and neuraminidase antigens in combination with a particular chitosan derivative, it is possible to achieve good IgG and good IgA responses. More particularly , the present Applicants have now found that if a chitosan is co-administered intranasally with influenza antigens such as the neuraminidase and haemagglutinin antigens, or if a host is predosed with a chitosan prior to administration of influenza antigens, good systemic and local immune responses are produced.

Chitosans are derivatives of chitin or poly-N-acetyl-D-glucosamine in which the greater proportion of the N-acetyl groups have been removed through hydrolysis.

Chitosans have previously been used in pharmaceutical formulations and are disclosed in EP-A-0460020 as mucosal absorption enhancers, However, EP-A-0460020 does not disclose or suggest that the chitosan could provide an adjuvant effect when administered in a vaccine composition.

Accordingly, in a first aspect, the invention provides a vaccine composition in the form of a kit comprising a first container containing an antigenic preparation comprising influenza antigen or antigens; and a second container containing an effective adjuvant amount of a chitosan.

The influenza antigens can be, for example, inactivated whole influenza virus, or purified or partially purified antigens. In an alternative embodiment, the influenza antigens can be present in a carrier molecule, for example as part of a fusion protein.

The antigenic preparation preferably contains haemagglutinin and neuraminidase influenza virus antigens. More particularly, the antigenic preparation preferably is inactivated whole influenza virus (WIV) or a composition containing purified haemagglutinin and neuraminidase influenza virus antigens.

Where a purified haemagglutinin and meuraminidase composition is employed, it is preferred that the purified haemagglutinin and neuraminidase antigens are present in the form of rosettes. The rosettes preferably are particles with a radius in the range 10 to 25 nanometres. It is preferred that the rosettes are substantially free of lipid and, moreover, it is preferred that the purified haemagglutinin and neuraminidase antigen preparation as a whole is substantially free of lipids.

An example of a haemagglutinin/neuraminidase preparation suitable for use in the compositions of the present invention is the "Fluvirin" product manufactured and sold by Evans Medical Limited of Speke, Merseyside, United Kingdom, and see also S. Renfrey and A. Watts, Vaccine, 1994, Volume 12, Number 8, pp 747–752.

Whole influenza virus vaccines can be prepared from killed influenza virus strains in known fashion. As will be appreciated, such inactivated whole virus preparations are a precursor to the purified preparations described above.

The vaccine compositions of the invention are preferably adapted for delivery to a mucosal surface, and most preferably are adapted for oral or intranasal delivery.

Preferably the chitosan used in the compositions of the invention is water-soluble.

The chitosan may advantageously be a deacetylated chitin which is at least 75% and preferably is at least 80% deacetylated. More preferably the chitosan is at least 85% de-acetylated, and particularly preferably is 88% to 90% de-acetylated.

A particular de-acetylated chitosan is the "Sea Cure G210" chitosan (Poly D-glucosamine hydroglutamate) available from Pronova Biopolymer of Drammen, Norway. This chitosan which is in the form of its glutamate derivative, has >80% deacetylation.

In a further aspect, the invention provides a method of immunising a host against infection with influenza, which method comprises administering to the host:

(i) from a first container an antigenic preparation comprising an influenza virus antigen or antigens as hereinbefore defined and (ii) from a second container an effective adjuvant amount of a chitosan as hereinbefore defined.

The contents of the first and second containers can be administered at substantially the same time, ie simultaneously or within a few minutes of each other, or they may be administered at spaced intervals. For example, the host may be pre-dosed with the chitosan and the antigenic preparation administered subsequently.

The first and second containers can be entirely separate or can be constituted by separate chambers of the same applicator device. Where the containers are separate, they could be provided in the form of a kit comprising first and second aerosol dispensers, or first and second syringes, by way of example. Where the first and second containers form part of the same applicator, they could for example, be defined by two barrels of a multibarrel syringe. Such applicators containing an influenza antigenic preparation in one chamber and a chitosan composition in another chamber form a further aspect of the invention.

In a further aspect, the invention provides a method of inducing a protective mucosal immune response and a systemic immune response by administering to a patient (i) from a first container an antigenic preparation comprising an influenza virus antigen or antigens as hereinbefore defined and (ii) from a second container an effective adjuvant amount of a chitosan as hereinbefore defined.

In a still further aspect, the invention provides a method of inducing a protective IgA mucosal immune response and an IgG systemic immune response by administering to a patient (i) from a first container an antigenic preparation comprising an influenza virus antigen or antigens, and (ii) from a second container an effective adjuvant amount of a chitosan, wherein the antigenic preparation and chitosan are as hereinbefore defined.

In another further aspect, the invention provides a method of enhancing the immune response of influenza virus antigens by co-administering therewith from a separate container a chitosan as hereinbefore defined.

The compositions of the invention can be presented for administration by a number of routes but preferably they are presented for administration mucosally, and in particular intranasally. Intranasal compositions can be formulated for example as liquids or dry powders, for administration as aerosols or drops.

Compositions for administration as nasal drops may contain one or more excipients of the type usually included in such compositions, for example preservatives, viscosity adjusting agents, tonicity adjusting agents, buffering agents and the like.

The present invention also contemplates the provision of means for dispensing intranasal formulations of influenza virus antigens and chitosan. A dispensing device may, for example, take the form of an aerosol delivery system, and may be arranged to dispense only a single dose, or a multiplicity of doses. Thus the first and second containers may be adapted for use in an aerosol dispensing device.

The antigenic preparation will be administered to the patient in an amount effective to stimulate a protective immune response in the patient. For example, the antigenic preparation may be administered to humans in one or more doses, each dose containing 1–250 microgrammes and more preferably 1–50 microgrammes of protein prepared from each virus strain. For example, where haemagglutinin and neuraminidase preparations are prepared from three virus strains, e.g. 2×Influenza A and 1×Influenza B, a total dose of viral protein administered could be in the range 3–150 microgrammes.

The invention will now be illustrated, but not limited, by reference to the drawings and the following examples.

EXAMPLE 1 PREPARATION OF CHITOSAN FORMULATION

Figure 1:
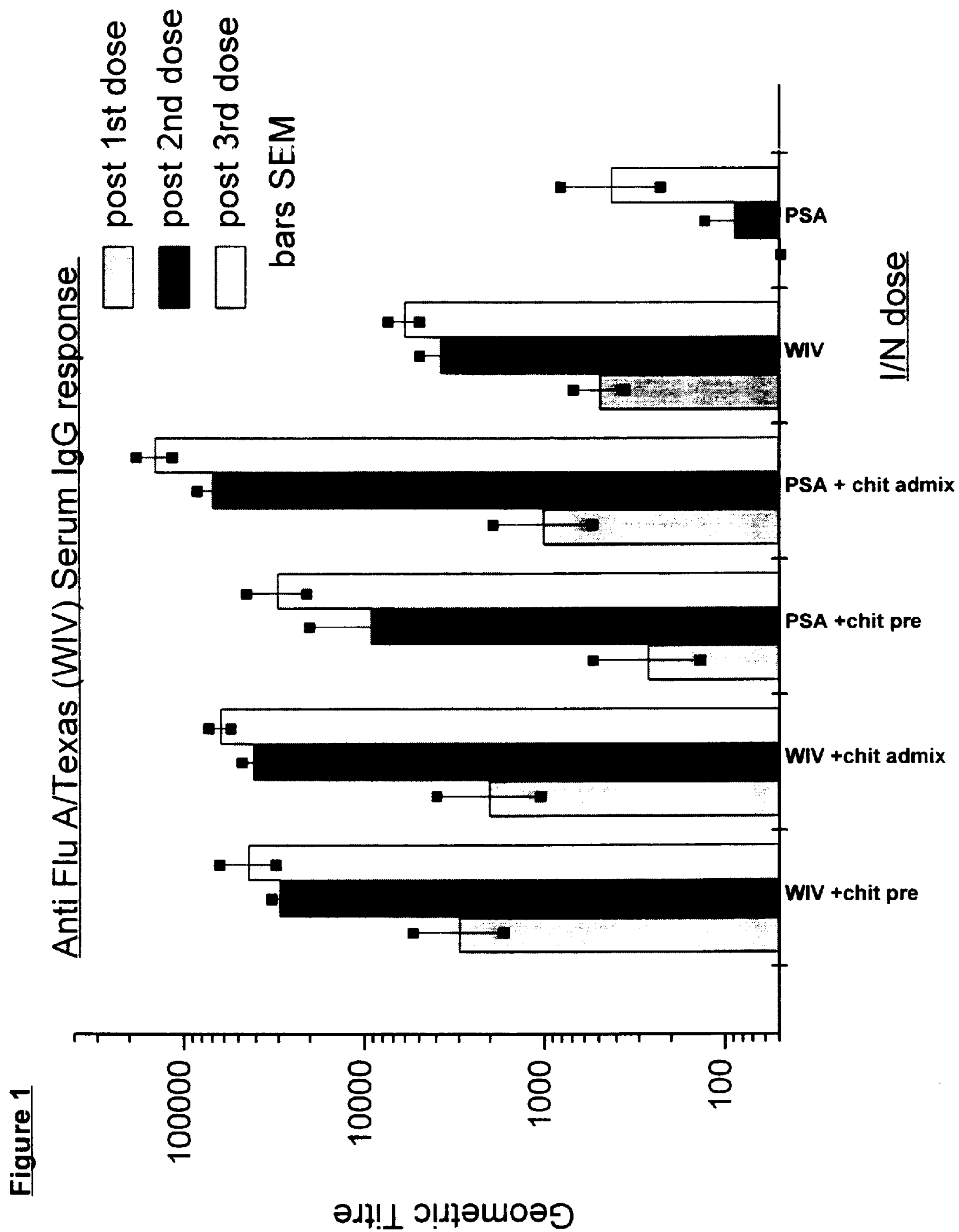
FIG. 1 illustrates the serum IgG anti-haemagglutinin response in mice immunised with inactivated whole influenza A/Texas (WIV). Each bar represents the log geometric mean titre of five mice. The error bars represent 1 standard error of the geometric mean.

A solution of 1 % chitosan glutamate, a medium viscosity de-acetylated chitin having greater than 80% deacetylation, was prepared by dissolving the chitosan glutamate in 0.5% W/V sodium chloride by stirring at room temperature for 48 to 60 hours. The pH of the resulting solution was increased to 5.8–6.0 using 0.1M $Na_2HPO_4$. The grade of chitosan glutamate used was a medium viscosity grade sold under the trade name "Sea Cure+G210" (Product Code 27150210), by Pronova Biopolymer of Drammen, Norway.

EXAMPLE 2 PREPARATION OF INFLUENZA ANTIGENIC FORMULATIONS

Purified Surface Antigen (PSA)

2A. Influenza purified surface antigen (PSA) containing Influenza A/Texas protein, available from Evans Medical Limited, Speke, Merseyside, United Kingdom, was made up in phosphate buffered saline (PBS) to give a protein concentration of approximately 1 mg/ml. The PSA consists almost entirely of the spike protein haemagglutinin (HA), although it does contain some neuraminidase.

WHOLE INFLUENZA VACCINE (WIV)

2B. Whole influenza vaccine (WIV) of the A/Texas strain was made up to 1mg/mi protein concentration in PBS.

EXAMPLE 3

Preparation of a Chitosan/Influenza Admixture

A 1:1 mixture of the chitosan glutamate solution and the PSA or WIV solution was prepared to give an intranasal vaccine composition containing 0.5% chitosan glutamate and 0.5 mg/ml influenza antigen.

Control solutions containing the same concentrations of WIV or PSA but not chitosan glutamate, were also prepared.

EXAMPLE 4

Mice Immunisation Studies

The compositions prepared as described in the Examples above were administered to groups of five adult (6–8 weeks) female BALB/c mice as follows:

| Group | Formulation | Dose/mice (total protein) |
|---|---|---|
| A | WIV + chitosan (separate administration) | 10 μg |
| B | WIV + chitosan (admixture) | 10 μg |
| C | PSA + chitosan (separate administration) | 10 μg |
| D | PSA + chitosan (admixture) | 10 μg |
| E | WIV (A/Texas) | 10 μg |
| F | PSA (A/Texas) | 10 μg |

Immunisations were given intranasally in 20 μl volumes (10 μl per nostril) to the mice in groups B, D, E, F. The group B and D mice received the preparations described in Example 3 above, whilst the group E and F control mice received the formulations of Examples 2B and 2A respectively and no chitosan. The mice in groups A and C first received 5 μl per nostril of the chitosan composition of Example 1 and then, following a recovery time of 4 minutes, were given 5 μl per nostril of the influenza formulations of Examples 2B and 2A respectively. The immunisation and sampling regime used is shown in Table 1.

TABLE 1

Immunisation and sampling regime

| Immunisation | Day | Sample | Day |
|---|---|---|---|
| 1 | 0 | 1 | 21 |
| 2 | 28 | 2 | 42 |
| 3 | 56 | 3 | 74 |

At sampling points 1 and 2, all mice from each group were sample bled. Sampling at sample point 3 was performed by cardiac puncture, following which the heads of the mice were removed and their nasal passages lavaged with 1 ml PBS+1 % bovine serum albumin.

Antibody and ELISPOT Assays

Figure 2:
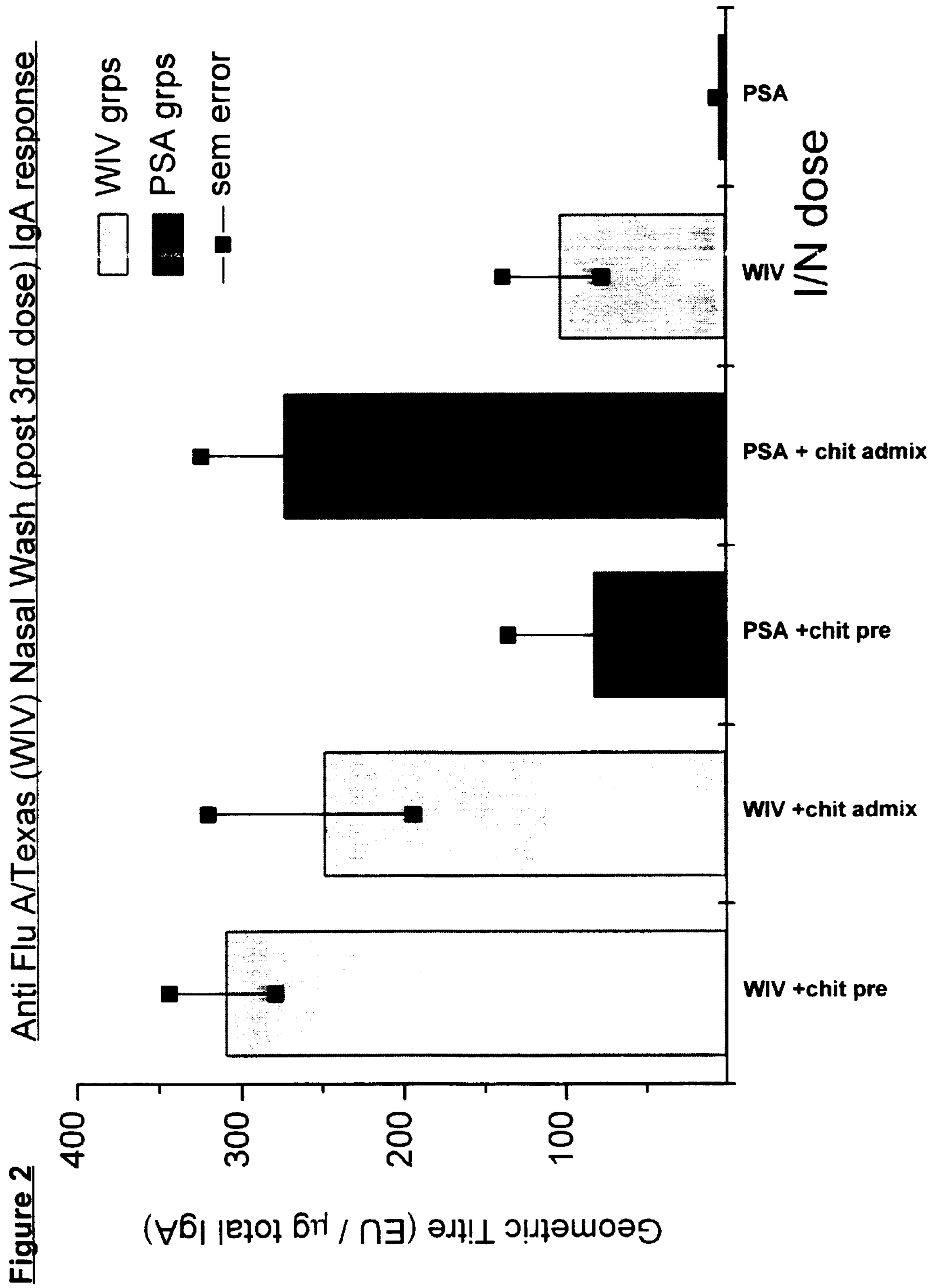
FIG. 2 illustrates the nasal IgA anti-influenza A/Texas/WIV response in mice immunised with WIV. As with FIG. 1, each bar represents the geometric mean titre of four mice, and the error bars represent 1 standard error of the geometric mean.

The immune responses stimulated by the immunisation regimes described above were analysed in conventional fashion using the ELISPOT and ELISA techniques. Thus, an Enzyme Linked Immunosorbant Assay (ELISA) was used to determine the serum IgG anti-A/Texas response, and the results are shown in FIG. 1 and Table 2 below. The ELISA technique was also used to determine the nasal IgA anti-A/Texas response and the results of this assay are shown in FIG. 2 and Table 3 below. In all assays whole influenza vaccine (WIV) was used as antigen. ELISA endpoint titres were calculated as sample dilutions yielding a result of 0.3 OD units for IgG and 0.1 OD units for IgA assay after background control (without sample) subtraction.

RESULTS

TABLE 2

Serum anti-WIV serum response (Table 2 and FIG. 1)

| Group | Post-Dose 1 | | Post-Dose 2 | | Post-Dose 3 | |
|---|---|---|---|---|---|---|
| | Seroconversion* | GMT+ | Seroconversion | GMT | Seroconversion | GMT |
| A. WIV + chitosan (separate) | 5/5 | 3005 | 5/5 | 29708 | 5/5 | 44338 |
| B. WIV + chitosan (admixture) | 5/5 | 2038 | 5/5 | 41426 | 5/5 | 63157 |
| C. PSA + chitosan (separate) | 4/5 | 271 | 5/5 | 9314 | 5/5 | 30599 |
| D. PSA + chitosan (admixture) | 5/5 | 1017 | 5/5 | 69331 | 5/5 | 144224 |
| E. WIV (A/Texas) | 5/5 | 499 | 5/5 | 3800 | 5/5 | 6044 |
| F. PSA (A/Texas) | 0/5 | 49 | 2/5 | 89 | 4/4 | 428 |

*No. positive/No. tested
+Geometric Mean Titre

Nasal IgA anti-WIV response

TABLE 3

Nasal IgA anti-A/Texas response EU/μg total IgA (Individual responses—geometric mean+sem)

| Group | Individual IgA Responses (EU/μg) | Geometric Mean (EU/μg) |
|---|---|---|
| A. WIV + chitosan (separate) | 342 351 405 240 246 | 310 ± 65 |
| B. WIV + chitosan (admixture) | 263 100 328 447 250 | 249 ± 126 |
| C. PSA + chitosan | 74 265 142 14 100 | 83 ± 52 |

-continued

| Group | Individual IgA Responses (EU/μg) | Geometric Mean (EU/μg) |
|---|---|---|
| (separate) | | |
| D. PSA + chitosan (admixture) | 283 199 289 193 490 | 274 ± 92 |
| E. WIV (A/Texas) | 52 89 156 67 254 | 104 ± 61 |
| F. PSA (A/Texas) | 7 9 5 4 | 6 ± 2 |

Figure 3A:
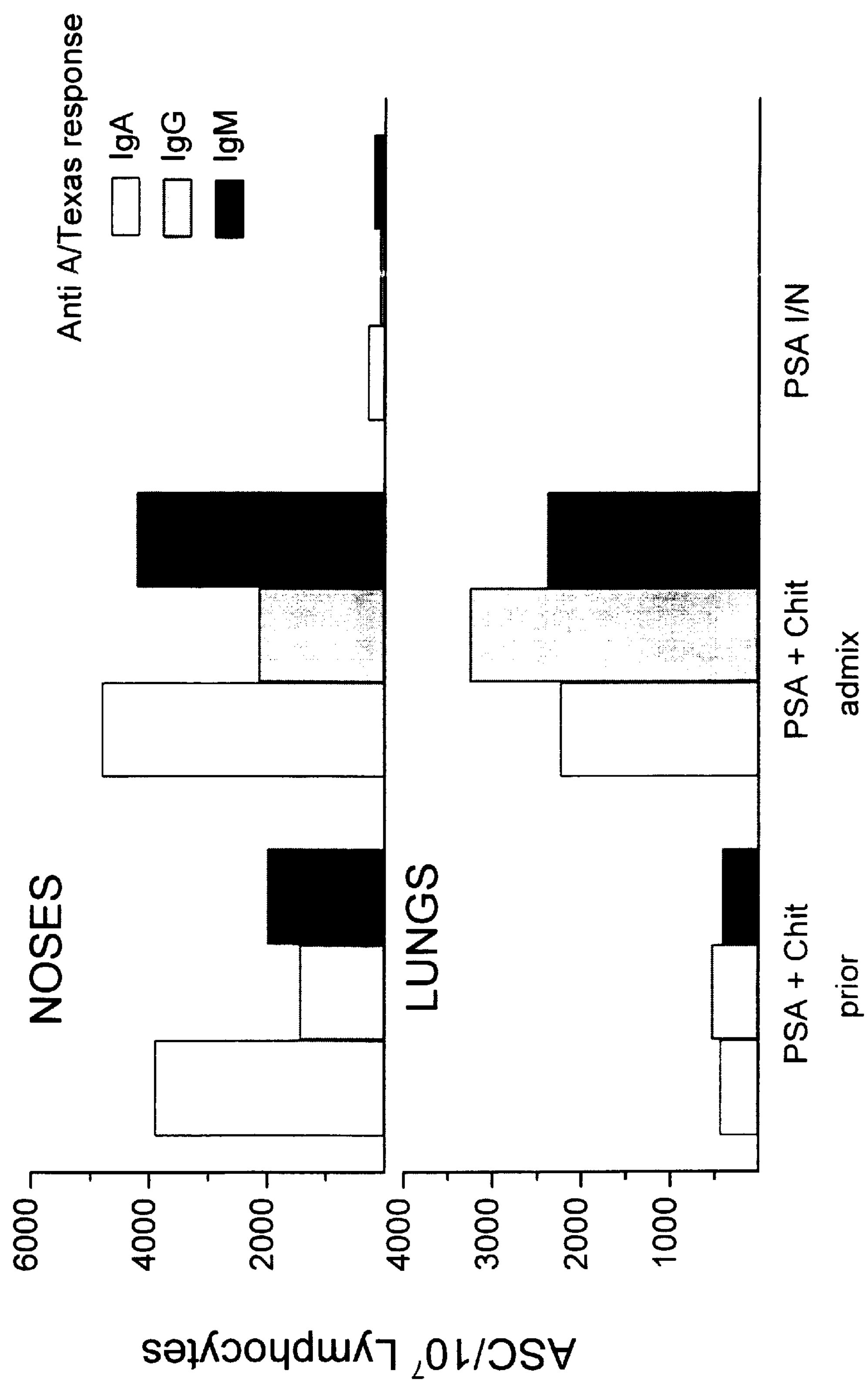
FIGS. 3*a* and 3*b* illustrate the determination of nasal and pulmonary WIV specific antibody secreting cells (ASC) in mice immunised with WIV, using ELISPOT.
Figure 3B:
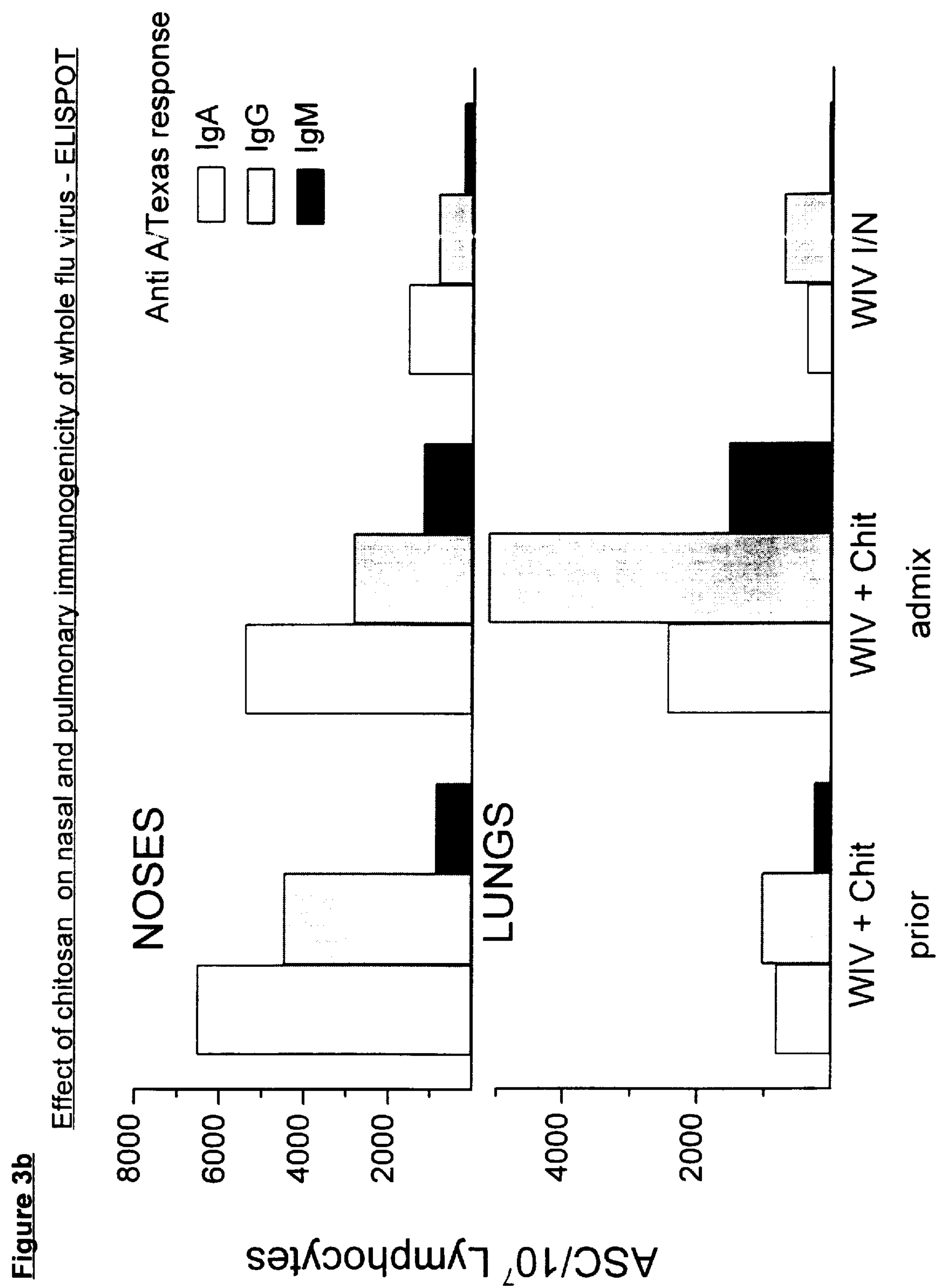

Antibody Secreting Cells (ASC) Specific for WIV in the Nasal and Pulmonary Mucosa Lymphocytes were isolated from the nasal mucosa and lung parenchyma of groups of five mice at the third sampling point. Lymphocytes from individual mice were pooled and assayed for cells secreting IgA, IgG and IgM anti-flu antibodies using ELISPOT. The results are shown in FIGS. 3*a* and 3*b*. In FIGS. 3*a* and 3*b*, the antibody secreting cells detected by the ELISPOT assay are expressed as the number of positive cells/$10^7$ total cells (lymphocytes). FIG. 3*a* illustrates the effect of chitosan on the nasal and pulmonary immunogenicity of the PSA preparation of Example 2A whereas FIG. 3*b* illustrates the effect of chitosan on the nasal and pulmonary immunogenicity of the WIV preparation of Example 2B. The results shown in FIGS. 3*a* and 3*b* illustrate that chitosan enhances the IgA ASC response to both PSA and WIV, the greater enhancement being observed with PSA. The strongest ASC responses were generated in the nasal mucosa with IgA ASC being dominant. Pulmonary responses were predominantly IgG secreting cells.

In general, greater ASC responses were induced by both PSA and WIV when they were formulated with chitosan, than when the chitosan was administered first. In the case of the IgA ASC response, the formulation containing both PSA and chitosan produced a greater response than was obtained when chitosan was administered first. However, there was no significant difference between the IgA ASC responses induced by the formulation containing both WIV and chitosan, and WIV preceded by the chitosan.

The results set out above illustrate that good immune responses can be obtained by administering influenza antigens and chitosans separately via the mucosal route. This offers an advantage in that it enables the potential problems associated with administration by injection to be avoided.

The aforementioned examples are merely exemplary of the present invention and are not intended in any way to limit the scope of the invention which is defined solely by the claims appended hereto.

What is claimed is:

1. A kit for providing an influenza vaccine, said kit comprising:

a first container containing an antigenic preparation comprising influenza antigen or antigens; and a second container containing an effective adjuvant amount of a chitosan, wherein the chitosan is a deacetylated chitin which is at least 80% deacetylated.

2. A kit according to claim 1 wherein the antigenic preparation in the first container comprises haemagglutinin and neuraminidase influenza antigens.

3. A kit according to claim 2 wherein the antigenic preparation in the first container is a whole influenza virus preparation.

4. A kit according to claim 2 wherein the antigenic preparation in the first container comprises purified haemagglutinin and neuraminidase influenza antigens.

5. A kit according to claim 4 wherein the purified haemagglutinin and neuraminidase influenza antigens are present in the form of rosettes having a radius in the range 10 to 25 nanometers.

6. A kit according to claim 1 wherein the antigenic preparation and the chitosan are adapted for mucosal administration.

7. A kit according to claim 6 wherein the antigenic preparation and the chitosan are adapted for intranasal administration.

8. A kit according to claim 6 wherein the antigenic preparation and the chitosan are adapted for oral administration.

9. A kit according to claim 1 wherein the chitosan is at least 85% deacetylated.

10. A kit according to claim 9 wherein the chitosan is 88% to 90% deacetylated.

11. A kit according to claim 1 wherein the chitosan is water-soluble.

12. A kit according to claim 1 wherein the chitosan is present in the second container in a solution which has a pH in the range 5.5 to 6.5.

13. A kit according to claim 12 wherein the pH of the chitosan solution is approximately 5.8–6.

14. A kit according to claim 1 wherein the first and second containers are adapted to cooperate with a dispenser for administering the contents thereof intranasally.

15. A kit according to claim 1 wherein the first and second containers are constituted by separate chambers in the same dispensing device.

16. A kit according to claim 15 wherein the first and second containers are constituted by two barrels of a multibarrel syringe.

17. A pharmaceutical product for providing an intranasal influenza vaccine, said product comprising:

a dispensing device adapted to deliver an intranasal pharmaceutical dosage; and a kit for providing an intranasal influenza vaccine, said kit comprising:

a first container containing an antigenic preparation comprising influenza antigen or antigens; and a second container containing an effective adjuvant amount of a chitosan, wherein the chitosan is a deacetylated chitin which is at least 80% deacetylated, wherein said antigenic preparation and said chitosan are adapted for intranasal administration.

18. A pharmaceutical product according to claim 17 wherein the dispensing device is an aerosol delivery system.

19. A method of immunising a host against infection with influenza, which method comprises separately administering to the host:

(i) from a first container an antigenic preparation comprising an influenza virus antigen or antigens, and (ii) from a second container an effective adjuvant amount of a chitosan wherein the chitosan is a deacetylated chitin which is at least 80% deacetylated.

20. A method of enhancing a protective IgA mucosal immune response and an IgG systemic immune response by administering to a patient (i) from a first container an antigenic preparation comprising an influenza virus antigen or antigens, and (ii) from a second container an effective adjuvant amount of a chitosan, wherein the chitosan is a deacetylated chitin which is at least 80% deacetylated.

21. A method of enhancing the immune response of influenza virus antigens, when administered to a patient intranasally, by co-administering therewith from a separate container a chitosan, wherein the chitosan is a deacetylated chitin which is at least 80% deacetylated.

* * * * *